(12) United States Patent
Brewer (10) Patent No.: US 7,151,914 B2
(45) Date of Patent: Dec. 19, 2006

(54) TRANSMITTER SYSTEM FOR WIRELESS COMMUNICATION WITH IMPLANTED DEVICES

(75) Inventor: Samuel Joseph Brewer, Anaheim, CA (US)

(73) Assignee: Medtronic, Inc., Minneapolis, MN (US)

(*) Notice: Subject to any disclaimer, the term of this patent is extended or adjusted under 35 U.S.C. 154(b) by 1384 days.

(21) Appl. No.: 09/932,957

(22) Filed: Aug. 21, 2001

(65) Prior Publication Data

US 2003/0040291 A1    Feb. 27, 2003

(51) Int. Cl.
*H01Q 11/12* (2006.01)

(52) U.S. Cl. ............... 455/127.1; 455/117; 455/522

(58) Field of Classification Search ............ 455/127.1, 455/127.2, 127.3, 117, 126, 522, 108, 95, 455/100, 120, 73, 87, 77, 121, 107, 123, 455/574, 343.1, 343.2, 343.3, 343.4, 343.5; 370/311; 600/485; 128/903; 607/59, 60, 607/61, 101, 32, 33, 72, 58, 46; 375/295; 331/165, 166, 167, 179; 333/17.3
See application file for complete search history.

(56) References Cited

U.S. PATENT DOCUMENTS

| | | | |
|---|---|---|---|
| 4,735,204 A | 4/1988 | Sussman et al. | |
| 4,784,142 A | 11/1988 | Liss et al. | |
| 4,803,988 A | 2/1989 | Thomson | |
| 4,813,418 A | 3/1989 | Harris | |
| 4,977,895 A | 12/1990 | Tannenbaum | |
| 5,002,053 A | 3/1991 | Garcia-Rill et al. | |
| 5,014,705 A | 5/1991 | Graupe et al. | |
| 5,052,391 A | 10/1991 | Silberstone et al. | |
| 5,081,989 A | 1/1992 | Graupe et al. | |
| 5,092,329 A | 3/1992 | Graupe et al. | |
| 5,117,826 A | 6/1992 | Bartelt et al. | |
| 5,143,089 A | 9/1992 | Alt | |
| 5,170,496 A * | 12/1992 | Viereck | 455/121 |
| 5,215,086 A | 6/1993 | Terry, Jr. et al. | |
| 5,314,458 A | 5/1994 | Najafi et al. | |
| 5,330,515 A | 7/1994 | Rutecki et al. | |
| 5,335,657 A | 8/1994 | Terry, Jr. et al. | |
| 5,354,320 A | 10/1994 | Schaldach et al. | |
| 5,370,672 A | 12/1994 | Fowler et al. | |
| 5,387,231 A | 2/1995 | Sporer | |
| 5,417,719 A | 5/1995 | Hull et al. | |
| 5,423,877 A | 6/1995 | Mackey | |
| 5,443,486 A | 8/1995 | Hrdlicka et al. | |

(Continued)

OTHER PUBLICATIONS

North et al., "Spinal cord stimulation for chronic intractable pain," Spinal Cord Stimulation II, pp. 49-63, Darmstadt, Steinkopff, 1995.

(Continued)

*Primary Examiner*—Aung Moe
(74) *Attorney, Agent, or Firm*—Shumaker & Sieffert, PA (57) ABSTRACT

A transmitter system for wireless communication with implanted medical devices includes a transmitter circuit having a resonant network the resonant frequency of which is adjusted by a feedback circuit in order to minimize the current drain from the power source and maximizing the power source life. The transmitter system may be powered by a power supply block which uses commonly available RS-232 signals of a host computer as a raw power source, combined with a high value storage capacitor to provide power for the wireless medical data programmer. A feedback circuit monitors the charging current as well as voltage impressed across the storage capacitor in order to maintain the charging current at maximum level during the charging time and in order to stop the charging once the full charge of the storage capacitor has been reached.

29 Claims, 8 Drawing Sheets

U.S. PATENT DOCUMENTS

| | | | |
|---|---|---|---|
| 5,458,625 | A | 10/1995 | Kendall |
| 5,458,626 | A | 10/1995 | Krause |
| 5,466,246 | A | 11/1995 | Silvian |
| 5,540,730 | A | 7/1996 | Terry, Jr. et al. |
| 5,569,166 | A | 10/1996 | Stone |
| 5,643,329 | A | 7/1997 | Solomonow et al. |
| 5,643,330 | A | 7/1997 | Holsheimer et al. |
| 5,702,429 | A | 12/1997 | King |
| 5,716,377 | A | 2/1998 | Rise et al. |
| 5,725,564 | A | 3/1998 | Freed et al. |
| 5,843,139 | A | 12/1998 | Goedeke et al. |
| 5,938,690 | A | 8/1999 | Law et al. |
| 5,999,857 | A * | 12/1999 | Weijand et al. ............... 607/60 |
| 6,206,835 | B1 * | 3/2001 | Spillman et al. ............ 600/485 |
| 6,308,102 | B1 | 10/2001 | Sieracki et al. |
| 6,343,222 | B1 * | 1/2002 | Jones ......................... 455/574 |
| 6,442,434 | B1 * | 8/2002 | Zarinetchi et al. ............ 607/61 |
| 6,654,642 | B1 | 11/2003 | North et al. |
| 6,665,525 | B1 * | 12/2003 | Dent et al. ................ 455/127.2 |
| 6,772,011 | B1 * | 8/2004 | Dolgin ......................... 607/61 |
| 7,005,935 | B1 * | 2/2006 | Moore ......................... 331/166 |

OTHER PUBLICATIONS

North et al., "Artificial Neural Networks: Application to Electrical Stimulation of the Nervous System," (abstract) Stereotactic and Functional Neurosurgery 65:161, 1995.

North et al., "Artificial Neural Networks: application to electrical stimulation of the human nervous system," Neurosurgical Focus 2(1:1):1-5, 1997.

North et al., "Patient-Interactive, Microprocessor-Controlled Neurological Stimulation System," Neuromodulation 1(4):185-193, 1998.

Fowler, K.R., "Neurological Stimulation System", Proceedings AAMI 21st Annual Meeting, Apr. 12-16, 1986, p. 27.

North et al., "Spinal Card Stimulation for Chronic, Intractable Pain: Experience over Two Decades Clinical Study," Neurosurgery, vol. 32, No. 3, pp. 384-395, 1993.

North et al., "Spinal cord stimulation for chronic, intractable pain: superiority of 'multi-channel' devices," Pain, V44, 1991, pp. 119-130.

North et al., "Spinal Cord Stimulation for Chronic Pain," Functional Neurosurgery, vol. 6, No. 1, Jan. 1995, pp. 145-155.

North, R.B., "Spinal Cord Stimulation for Chronic, Intractable Pain," Electrical and Magnetic Stimulation of the Brain and Spinal Cord, 1993, pp. 289-301.

North, R.B., "The Role of Spinal Cord Stimulation in Contemporary Pain Management," APS Journal, vol. 2, No. 2, 1993, pp. 91-99.

Alo et al., "Computer Assisted and Patient Interactive Programming of Dual Octrode Spinal Cord Stimulation in the Treatment of Chronic Pain," Neuromodulation, vol. 1, No. 1, 1998 pp. 30-45.

Fowler et al., "Patient-interactive PC interface to implanted, multichannel stimulators," Proceedings of 39th Annual Conference on Engineering in Medicine and Biology, p. 380, 1986.

North et al., "Computer-Controlled, Patient-Interactive, Multichannel, Implanted Neurological Stimulators," Applied Neurophysiology 50:39-41, 1987.

North et al., Computer-controlled, multichannel, implanted neurological stimulation system: Clinical assessment, Pain (Suppl.) 5:S83, 1990.

Fowler et al., "Computer-Optimized Neurological Stimulation," Proc. Ann. Internat. Conf. IEEE Engineering Medicine and Biology Soc., vol. 13, No. 4, pp. 1692-1693, 1991.

Fowler et al., "Computer-Optimized Neurostimulation," APL Technical Digest vol. 12, No. 2, pp. 192-197, 1991.

North et al., "Patient-interactive, computer-controlled neurological stimulation system: clinical efficacy in spinal cord stimulator adjustment." Journal of Neurosurgery 76:967-972, 1992.

North et al., "Automated 'pain drawing' analysis by computer-controlled, patient-interactive neurological stimulation system," Pain 50:51-57, 1992.

North et al., "Computer-controlled, patient-interactive neurological stimulation system," (Abstract) Acta Neurochir 117:90, 1992.

North et al., "Patient-Interactive, Microprocessor-Controlled Neurological Stimulation System," (Abstract), Stereotactic and Functional Neurosurgery 62:309-315, 1994.

North et al., "Consensus Conference on the Neurosurgical Management of Pain," Neurosurgery 34:4, 756-761, 1994.

North et al., "A Prospective, Randomized Study of Spinal Cord Stimulation versus Reoperation for Failed Back Surgery Syndrome: Initial Results," Stereotact Funct Neurosurg 1994:62:267-272.

North et al., "Prognostic Value of Psychological Testing in Patients Undergoing Spinal Cord Stimulation: A Prospective Study," Neurosurgery, vol. 39, No. 2, 1996.

North et al., "Specificity of diagnostic nerve blocks: a prospective, randomized study of sciatica due to lumbosacral spine disease," Pain, 65, pp. 77-85, 1996.

North et al., "Automated, Patient-Interactive, Spinal Cord Stimulator Adjustment: A Randomized Controlled Trial," Neurosurgery 52:572-580, 2003.

Khalessi et al., "Automated, patient-interactive spinal cord stimulator adjustment: A cost-minimization analysis," Neurosurgery, vol. 53, No. 2, pp. 501-502, 2003.

* cited by examiner

TRANSMITTER SYSTEM FOR WIRELESS COMMUNICATION WITH IMPLANTED DEVICES

FIELD OF THE INVENTION

The present invention relates to digital signal transmission systems, and more particularly to transmitter systems for wireless communication with medical electrical devices implantable into a human body.

In more particularity, the present invention relates to a transmitter system powered by a battery, where the resonant frequency of the transmitter circuit is constantly adjusted to minimize the current consumed by the transmitter circuit in order to extend the battery life.

Further, the present invention relates to a transmitter system powered by a discharge current of a storage capacitor which is charged with commonly available signals supplied to the storage capacitor via the serial port of a host computer. A feedback circuit is employed which keeps the current charging the storage capacitor at a pre-set maximum level for the duration of the charging time, to permit the use of the full voltage supplied by the host computer in the least amount of time possible to charge the storage capacitor.

Additionally, the present invention is directed to a transmitter system for programming medical electrical devices implanted into a human body which may use as a power source either (1) a battery along with a novel scheme for extending the useful battery life; or alternatively, (2) a discharge current of a storage capacitor charged with signals obtained from a host computer where a feedback circuit is employed providing for charging the storage capacitor in the least possible charging time consuming substantially the full potential supplied by the host computer.

BACKGROUND OF THE INVENTION

Implanted neurostimulators are used to stimulate neural tissue to treat pain. By means of neurostimulation it is possible to block the pain indicating signals which travel to the brain. Electric pulses are passed between metal electrode contacts implanted into the human body and through the intervening neural tissue. The implanted neurostimulators, in order to be effective in pain treatment are adapted to be controlled by either switching the implanted device on/off, changing the amplitude and frequency of neuro-stimulation, or generating a specific stimulus pattern.

In order to control the implanted neurostimulators a wireless data transmission is commonly used where the implanted neurostimulators communicate bi-directionally with external devices through low frequency electromagnetic transmissions. Typically, a device, external to the human body, acts as a programmer for the implanted device by transmitting radio frequency codes to the implanted device to program its operation.

Such transmitters are typically powered by batteries. Maximum efficiency of the transmitter depends upon generating the largest current through a transmitter antenna coil while consuming the minimum current drained from the battery or other power source. To provide for the efficient low power operation of the transmitter, a high-Q resonant LC network in the transmitter circuit is generally employed. However, since some of the transmitters may be placed in close proximity to living tissue during operation, the external influences, such as human body capacitance and loading effects, may tend to de-tune a high-Q resonant LC network in the transmitter circuit, thus deteriorating the targeted low power operation of the transmitter circuit.

There has been a long lasting need in the field of neurostimulation a way in which to minimize, or completely remove the de-tuning effect of the external influences onto the transmitter circuit in order to achieve efficient low power operation thereof to maximize the useful battery life.

Another problem has existed in the field of wireless communication with implanted neurostimulation devices in that portable transmitters often depend upon either wall adapters or host equipment as power sources. In some cases, however, neither source is available for the transmission device. Additionally, for the wireless transmitter scheme high current pulses are often needed which exceed the capability of low power supplies such as batteries. Therefore, a novel power supply scheme for wireless medical data transmission, as an alternative to a battery, is desirable and long awaited in the field of the neurostimulation.

SUMMARY OF THE INVENTION

It is therefore an object of the present invention to provide a battery operated efficient transmitter system for medical data transmission substantially free of the de-tuning effects caused by external influences such as human body capacitance.

It is another object of the present invention to provide a battery operated transmitter where efficient low power operation is achieved by providing feedback control of the current consumed by the transmitter circuit in order to adjust resonating frequency of the resonant LC network in the transmitter circuit once the deviation of the consumed current from a predetermined optimal level has been sensed.

It is another object of the present invention to provide a battery operated transmitter system where the signal indicative of the current consumed by the transmitter circuit is read by an Analog-to-Digital converter. The output of the analog-to-digital converter is coupled to a microcontroller to supply thereto digital data corresponding to the sensed consumed current. In this manner, the microcontroller monitors the data and changes the resonant frequency of the LC network (LC tank and human body), thus reducing the current consumed by the transmitter circuit to a desired pre-set level.

It is still an object of the present invention to provide a transmitter system for wireless communication with implanted medical devices employing a power supply scheme which includes a high value storage capacitor, and uses a commonly available RS-232 signal of a host computer as a raw power source to charge the storage capacitor to full capacity in the least amount of time with minimal or zero losses of the voltage developed from the RS-232 signal.

It is a further object of the present invention to provide a novel power supply scheme for a wireless medical data transmission including a host computer and a storage capacitor where a feedback circuit is employed between the storage capacitor and the host computer which monitors the charging current supplied to the storage capacitor as well as the voltage impressed across the storage capacitor in order to maintain the charging current at a pre-set maximum level for the duration of the charging time, and in order to terminate charging once the voltage impressed across the storage capacitor reaches predetermined values.

According to the teachings of the present invention, a transmitter system for wireless communication with a medical device implanted into a human body, includes:

a transmitter circuit with a resonant network oscillating at a resonant frequency to generate signals for transmission to the medical device, a current sensing unit coupled to the transmitter circuit for sensing current consumed by the transmitter circuit, and a controller generating and outputting a drive signal to the transmitter circuit to control the resonance frequency thereof. The controller is coupled to the current sensing unit to monitor the sensed current and to change the drive signal to adjust the resonance frequency of the transmitter circuit once the sensed current exceeds a predetermined current value in order to minimize the current consumed by the transmitter circuit.

Preferably the current sensing unit in the subject transmitting system is an Analog-to-Digital converter and the controller is a microprocessor.

The transmitter circuit includes first and second pairs of switches forming an H-bridge coupled to the resonant network. The drive signal generated by the controller is fed to said switches of said H-bridge to control switching thereof which permits controlling the resonant frequency of the resonant network.

The drive signals include first pulses and second pulses generated with a time interval therebetween in a manner whereby the first pulses are fed to the first pair of switches and the second pulses are fed to the second pair of switches.

The interval between said first and second pulses corresponds to a natural resonance frequency of the resonant network when the sensed current remains below the predetermined current value. However, upon the sensed current exceeding the predetermined current value, the controller changes the interval between said first and second pulses to deviate the resonant frequency of the resonant network from the natural resonant frequency thereof to decrease the sensed current to the value below the predetermined current value.

The interval between the first and second pulses may be equal to sub-multiples of the natural resonant frequency.

The transmitter system of the present invention can be powered by a battery supplying current to the transmitter circuit, or, alternatively by a novel power supply block. The power supply block includes:

a current limit switching circuit coupled to the serial port of a host computer, a storage capacitor coupled between an output of the current limit switching circuit and said transmitter circuit (the storage capacitor being charged with charging current supplied from the host computer through the current limit switching circuit and the storage capacitor supplying discharging current therefrom to the transmitter circuit), and a feedback circuit coupled between the storage capacitor and the current limit switching circuit.

The feedback circuit preferably includes:

an analog-to-digital converter coupled to the storage capacitor to monitor the voltage across the storage capacitor and the charging current supplied thereto, and a microprocessor coupled between the output of the analog-to-digital converter and the current limit switching circuit. The microprocessor compares the monitored voltage across the storage capacitor and the charging current with a predetermined voltage limit value and the predetermined current limit value respectively, and switches the current limit switching circuit to an appropriate limiting resistor therein once the voltage limit value has been reached, or upon the current falling below the predetermined level.

Preferably, the microprocessor establishes a switching hysteresis to prevent switch chatter at the crossover points.

The transmitter system of the present invention may also combine the principles of low power operation and the principles of power supply block fed by signals from the host computer.

These and other novel features and advantages of the subject invention will be more fully understood from the following detailed description of the preferred embodiment in conjunction with the accompanying Drawings.

DESCRIPTION OF THE PREFERRED EMBODIMENT

Figure 1:
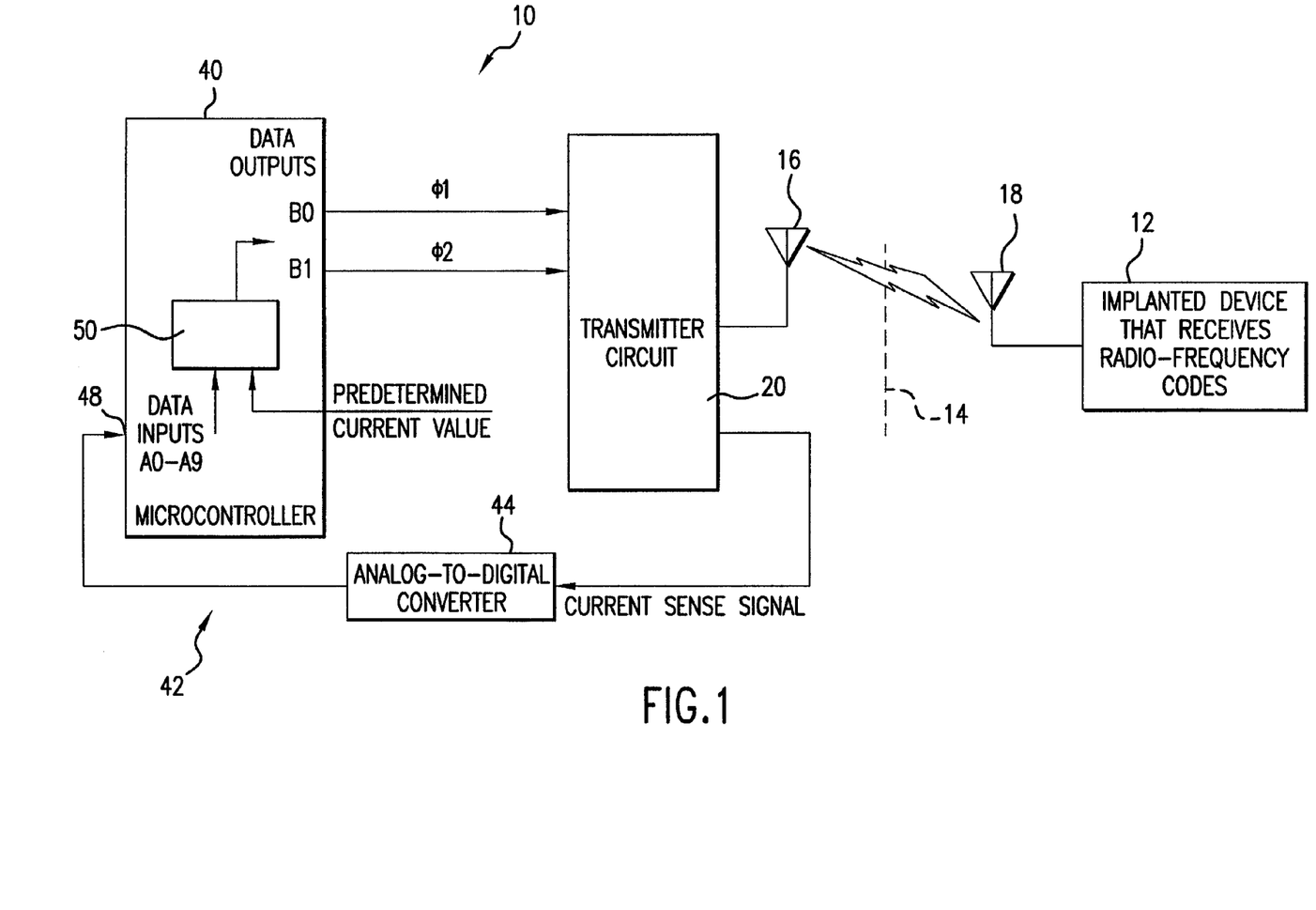
FIG. 1 is a block diagram of the transmitter system of the present invention.

Referring to FIG. 1, a transmitter system 10 of the present invention is positioned externally to an implanted device 12 and is separated therefrom by a barrier 14 which for a particular application of the transmitter system 10 are the tissues and skin of a human body, i.e., of a patient using the implanted device 12. For communication between the transmitter system 10 and the implanted device 12, the transmitter system 10 is provided with an antenna 16 which radiates a carrier signal modulated by an information signal towards antenna 18 of the implanted device 12.

The implanted device 12 may perform a plurality of functions, including tissue stimulation, sensing and monitoring the body parameters, as well as other parameters. Regardless of the type of function performed by the implanted device 12, it receives coded information, such as on/off switching, frequency and amplitude of stimulation, stimulation pattern, etc., from the transmitter system 10. Typically, transmitters for neurostimulation are formed as miniature "remote control" devices powered by a battery. It is of extreme importance to effectively use current provided by battery in order to extend the useful life thereof.

Figure 2:
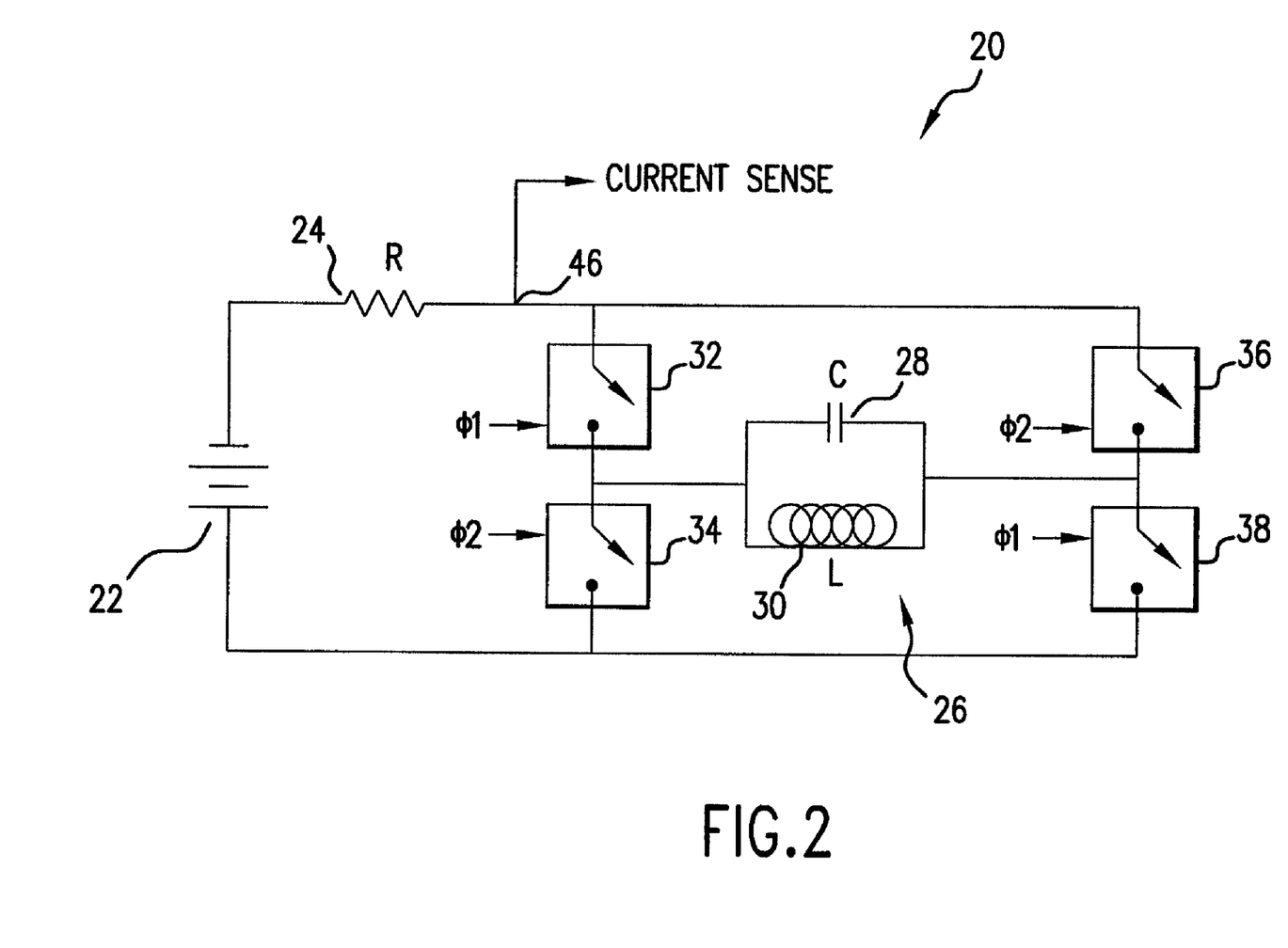
FIG. 2 is a detailed block diagram of the battery powered transmitter circuit of the present invention.

In order to provide efficient low power operation and maximize battery life, the transmitter system 10 of the present invention uses a pulse driven high-Q resonant LC network with feedback frequency control to generate a carrier signal which may transmit digital data using any form of amplitude modulation to the antenna 18 of the implanted device 12 for programming same. Referring to FIGS. 1 and 2, the transmitter system 10 of the present invention includes a transmitter circuit 20 which, as best shown in FIG. 2, is powered by a battery 22 supplying current through the resistor 24 to a high-Q LC tank 26 formed of a capacitor 28 and an inductive coil 30 coupled in parallel and which is parallel-resonant at a desired transmit frequency.

Four switches 32, 34, 36, and 38, which preferably are FET switches well known to those skilled in the art, are coupled to the LC tank 26 in a manner which forms an H-bridge. The micro-controller 40, best shown in FIG. 1, generates pulses φ1 and φ2 at an interval which correspond approximately to the natural resonant frequency of the LC tank 26 to drive the LC tank 26 to resonate and output a carrier signal which is further modulated and is sent to the antenna 18 of the implanted device 12. In this manner, the largest signal is generated through the coil 30 of the antenna 16 of the transmitter circuit 20 while consuming the minimum current drain from the battery 22, thus attaining the maximum efficiency of the transmitter system 10. However, since the transmitter circuit 20 is typically placed in the neighborhood of the patient's body for programming the implanted device 12, the body capacitance and other loading effects tend to de-tune the high-Q LC tank 26 since a new resonant network is formed which consists of the LC tank 26, the human body capacitance and other loading structures externally influencing the LC resonant tank 26.

The natural resonant frequency of newly formed network consisting of the LC tank 26 and the human body, is manually different from the natural resonant frequency of the LC tank 26 itself. In order to attain the maximum efficiency of the transmitter system 10, the transmitter circuit is to be operated at the natural resonant frequency of the newly formed resonant network. Since the parameters of the resonant network are subject to changes, for instance, when relative disposition of the transmitter and the human body alters, the resonant frequency of the resonant network must be constantly adjusted to provide oscillation of the resonant network at its natural resonant frequency.

For this purpose, the transmitter system 10 of the present invention is provided with a closed loop control of the transmitter circuit 20 to minimize battery current drain under the de-tuning condition. The feedback circuit 42, best shown in FIG. 1, includes an Analog-to-Digital converter 44 and the micro-controller 40. The ADC 44 is preferably a 10-bit Analog-to-Digital converter, which is coupled to the node 46 proximal to the resistor 24, best shown in FIG. 2, to measure the voltage drop across the resistor 24 which is proportional to the average current flowing into the resonant network. Thus, measuring the voltage drop across the resistor 24, the Analog-to-Digital converter 44 senses the average current flowing into the resonant network consisting of the LC tank 26 and the human body. Digital data corresponding to the average current in the resonant network are output from the Analog-to-Digital converter 44 and are supplied to the Data Input port 48 of the micro-controller 40. The firmware 50 within the micro-controller 40 monitors the digitized current sense signal supplied from the output of the Analog-to-Digital converter 44 and compares the same with a predetermined current value pre-set in the firmware 50. When the current sense signal exceeds the predetermined current value, an algorithm in the firmware 50 changes the repetition interval of the pulses Φ1 and Φ2 to minimize the current sense signal. Thus, the microprocessor 40 maintains optimum battery life by minimizing the current consumed by the transmitter circuit 20.

Figure 3:
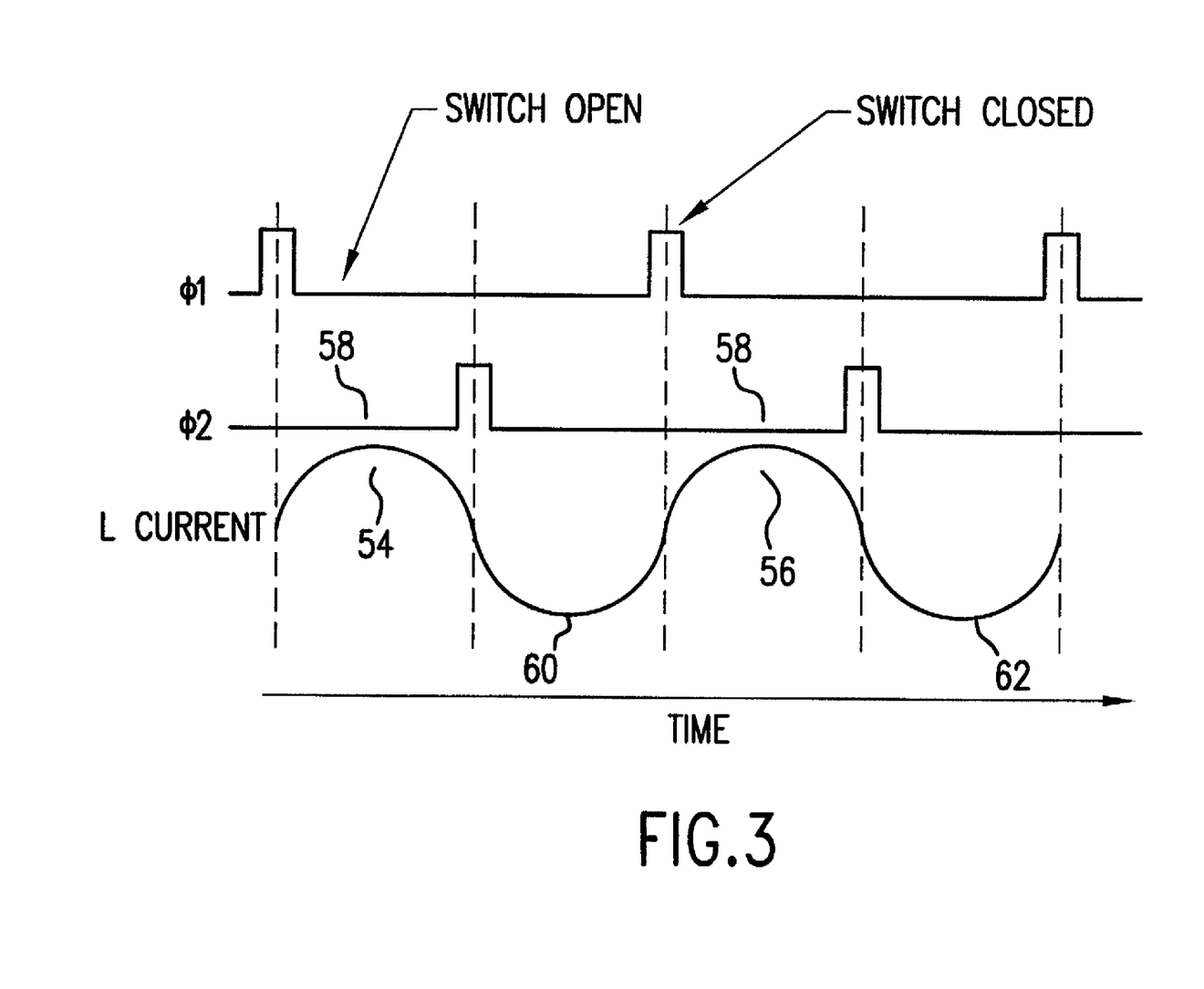
FIG. 3 is a timing diagram showing the correspondence between the carrier signal generated at the transmitter circuit and modulating pulses F1 and F2.

Referring to FIG. 3, showing the relative timing of the Φ1 and Φ2 pulses and the current flowing in the inductor coil 30, the micro-controller 40 generates pulses Φ1 and Φ2 at an interval which corresponds approximately to the natural resonant frequency of the resonant network formed by the LC tank 26 and the human body. By supplying the pulses Φ1 to the switches 32 and 38, while supplying the pulses Φ2 to the switches 34 and 36, the switches are closed for a brief period of time, typically one-fifth the pulse repetition interval, and remain open for the remainder of the time. While the associated pair of switches, for example switches 32 and 38, are closed (pulse Φ1 is supplied thereto), a small current flows into the parallel resonant network which sustains oscillation thereof as shown by half-waves 54 and 56 of FIG. 3. When the pulses Φ2 are output from the micro-controller 40 upon expiration of the interval 58 from the pulses Φ1, the resonant network generates half waves 60 and 62 (the switches 34 and 36 are closed).

By constantly adjusting the driving frequency (repetition rate of the pulses Φ1 and Φ2) to the natural resonant frequency of the resonant network, consisting of the LC tank 26 and human body minimum current will be consumed by the transmitter circuit 20 in order to generate the carrier signal consisting of the half waves 54, 56, 60 and 62. The generated carrier signal may transmit digital data using some form of amplitude modulation such as on-off keying, pulse position modulation, etc.

Further current drain reduction can be obtained by increasing the pulse repetition interval of pulses Φ1 and Φ2 to sub-multiple (½, ⅓, ¼, etc.) of the natural resonant frequency of the LC tank 26, depending upon how much amplitude variation in the carrier signal may be tolerated by the system using this technique.

Figure 4:
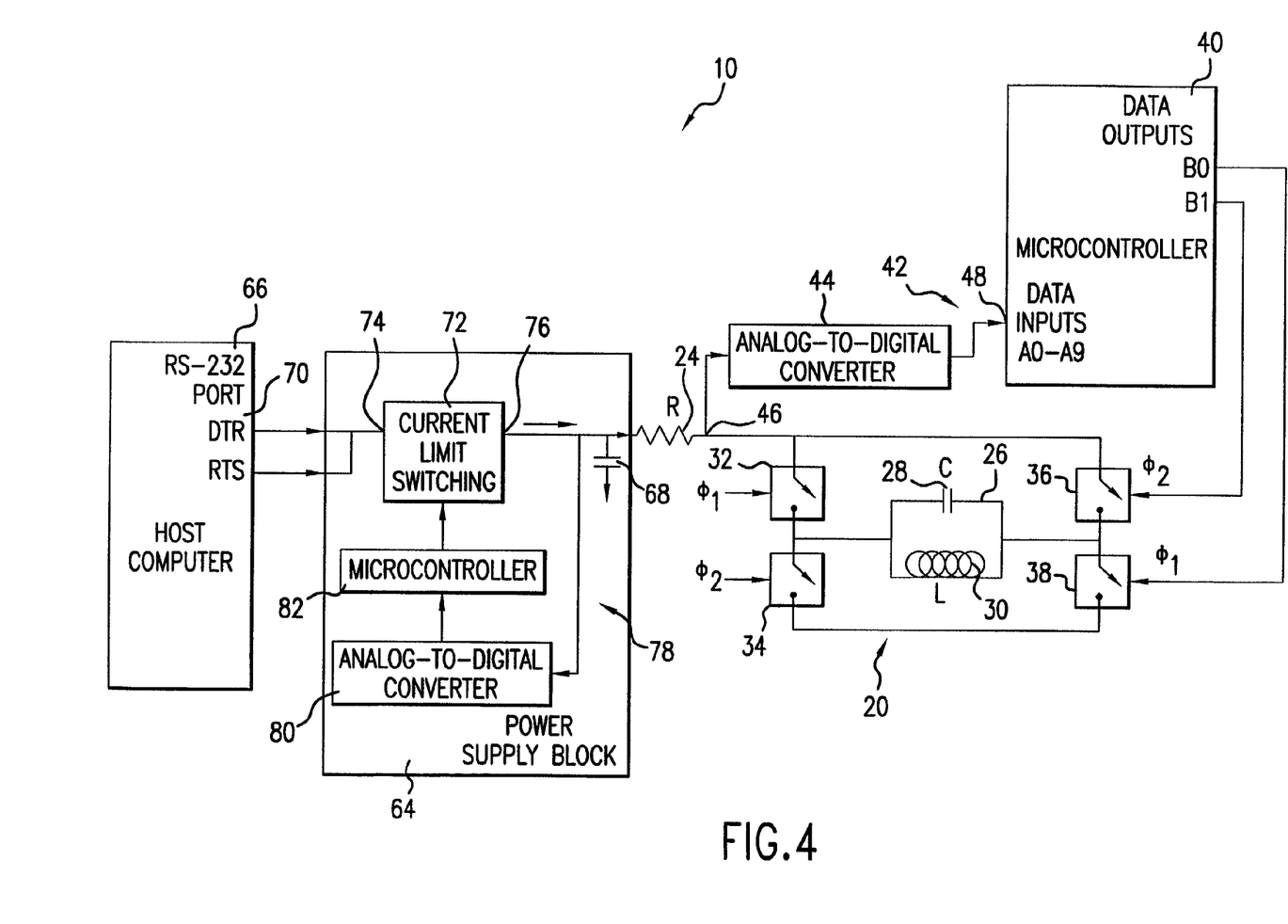
FIG. 4 is a block diagram of the transmitter system of the present invention showing the power supply block of the present invention.
Figure 5:
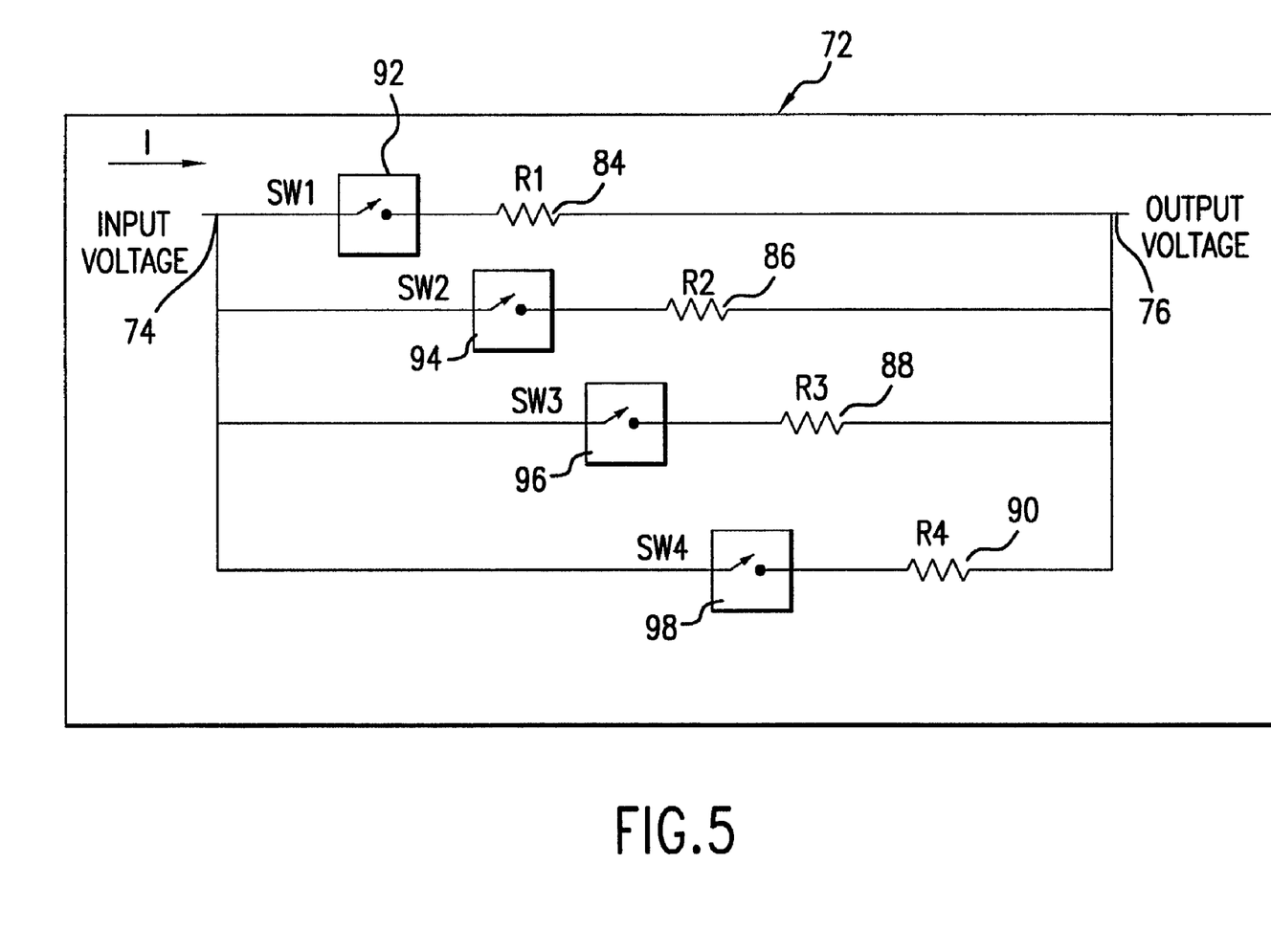
FIG. 5 is a detailed block diagram of the current switching circuit of the novel power supply block of the present invention.

Alternative to battery power, the transmission system of the present invention may be powered by power supply block 64 best shown in FIGS. 4 and 5. In a situation where wireless transmitter scheme needs high current pulses which exceed the capability of normal low power device supplies, such as batteries, or when neither wall adaptors nor host equipment as power sources is available, the power supply block 64 may be employed which uses, as a low power source, the RS-232 signals from a host computer 66 combined with a high value storage capacitor 68 to provide power for the wireless medical data programmer (transmitter system) 10 described in previous paragraphs and shown in FIGS. 1 and 2.

Referring to FIG. 4, the host computer 66 supplies power via the serial RS-232 port 70 to the power supply block 64. Both terminals, DTR (data terminal ready) and RTS (ready to send) of the host computer 66 are set to provide a continuous voltage, typically +5 Volts on most state-of-the-art computers. The power supply block 64 includes a current limit switching circuit 72 coupled to the host computer 66 to receive voltage therefrom at the input 74 thereof. The output 76 is coupled to the storage capacitor 68 in order to supply charging current thereto. In order to limit the time required to fully charge the storage capacitor 68, a feedback circuit 78 consisting of an Analog-to-Digital converter 80 and microprocessor 82 is coupled between the storage capacitor 68 and the current limit switching circuit 72. The Analog-to-Digital converter 80 senses the charging current supplied to the storage capacitor 68, digitizes the sensed current and provides the digital data corresponding to the sensed current to the microprocessor 82. The microprocessor 82 monitors the digital data supplied from the Analog-to-Digital converter 40 and compares the monitored sensed charging current with a pre-set maximum level of the charging current for the duration of the charging time for the storage capacitor 68. When the sensed charging current falls below the pre-set maximum level thereof, the microcontroller 82 switches the current limit switching circuit 72 (as will be described in following paragraphs) to adjust the charging current to a pre-set maximum level. By using this technique, it is possible to charge the storage capacitor 68 from the fully discharged state to the full potential supplied by the RS-232 interface in the least amount of time. Since this technique does not suffer voltage drops which would limit the ultimate voltage reached, the full voltage developed from the RS-232 signals is impressed across the storage capacitor 68.

As shown in FIG. 5, representing details of the current limit switching circuit 72, the latter includes four resistors 84, 86, 88, and 90, which are connected in parallel using switches 92, 94, 96, and 98 which are typical FET switches set at predetermined values. The resistor 90 is typically of 0 ohm value. Thus, when the microprocessor 82 determines that the charging current falls below the preset maximum level thereof, the microprocessor 82 switches into the circuit one or several resistors (by closing the respective switches 92–98) in order to increase the charging current.

Referring back to FIG. 4, the Analog-to-Digital converter 80 in addition to monitoring the charging current, monitors the voltage across the storage capacitor 68, and when the monitored voltage reaches a predetermined value, the appropriate resistor(s) of FIG. 5 will be switched into the circuit. The switching decision is made in the microprocessor 82 using an algorithm the flow chart diagram of which is presented in FIG. 6 and which compares the output voltage with preset limits and selects the appropriate current limiting resistor(s) using switches 92–98. As an added feature, some hysteresis may be built into the algorithm to prevent switch "chatter" at the crossover point.

Figure 6:
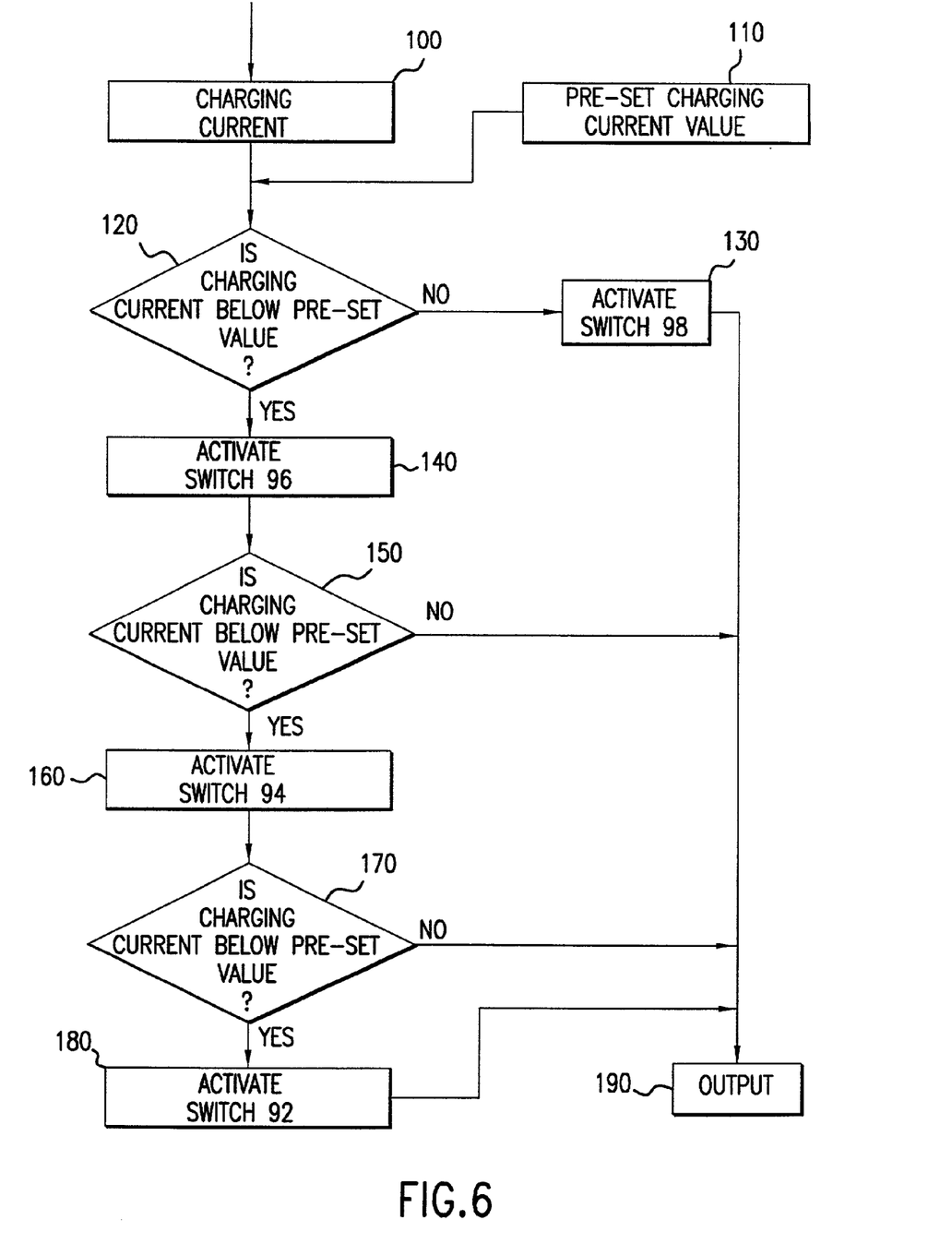
FIG. 6 is a flow chart diagram of the algorithm, in accordance with which the microprocessor selects appropriate limiting resistors.

As shown in FIG. 6, the charging current 100 is supplied for processing from the analog-to-digital converter 80 to the microcontroller 82. The microcontroller 82 contains a predetermined charging current value 110 preset therein for comparison with the charging current 100. The charging current 100 is compared with the preset charging current value 110 and the results of such a comparison are supplied to the logic block 120 "Is Charging Current Below Preset Value?". If the charging current is not below the preset value 110, the flow chart follows to the logic block 130 "Activate Switch 98". The activation of the switch 98, due to 0 ohm value of the limiting resistor 90, makes no changes to the charging current. If, however, the charging current is below the preset value 110, the logic flows to the block 140 "Activate Switch 96".

The microcontroller 82 monitors the charging current resulting from activating the switch 96, and compares it with the preset charging current 110 in block 150 "Is Charging Current Below a Preset Value?" If the charging current is not below the preset value, meaning that the appropriate limiting resistor has been switched in by the switch 96, the logic flows to the block 190 "Output". If, however, the charging current is still below the preset value 110, the flow chart follows to the block 160 "Activate Switch 94" to switch the limiting resistor 86 into the circuitry.

The logic continues to monitor the charging current resulting from such switching, and follows to the logic block 170 in which the resulting charging current obtained by switching the resistor 86 into the circuitry is compared with the preset charging current value 110. If, the charging current is higher than the preset charging current value 110, the logic flows to the "Output" block 190, meaning that the appropriate limiting resistor has been switched into the circuitry for maintaining the charging current above the preset charging current value 110. If, however, in the block 170, the charging current falls below the preset value 110, the logic follows to the block 180 "Activate Switch 92" to switch the limiting resistor 84 into the circuitry, and from the block 180 the logic flows to the "Output" block 190.

Figure 7:
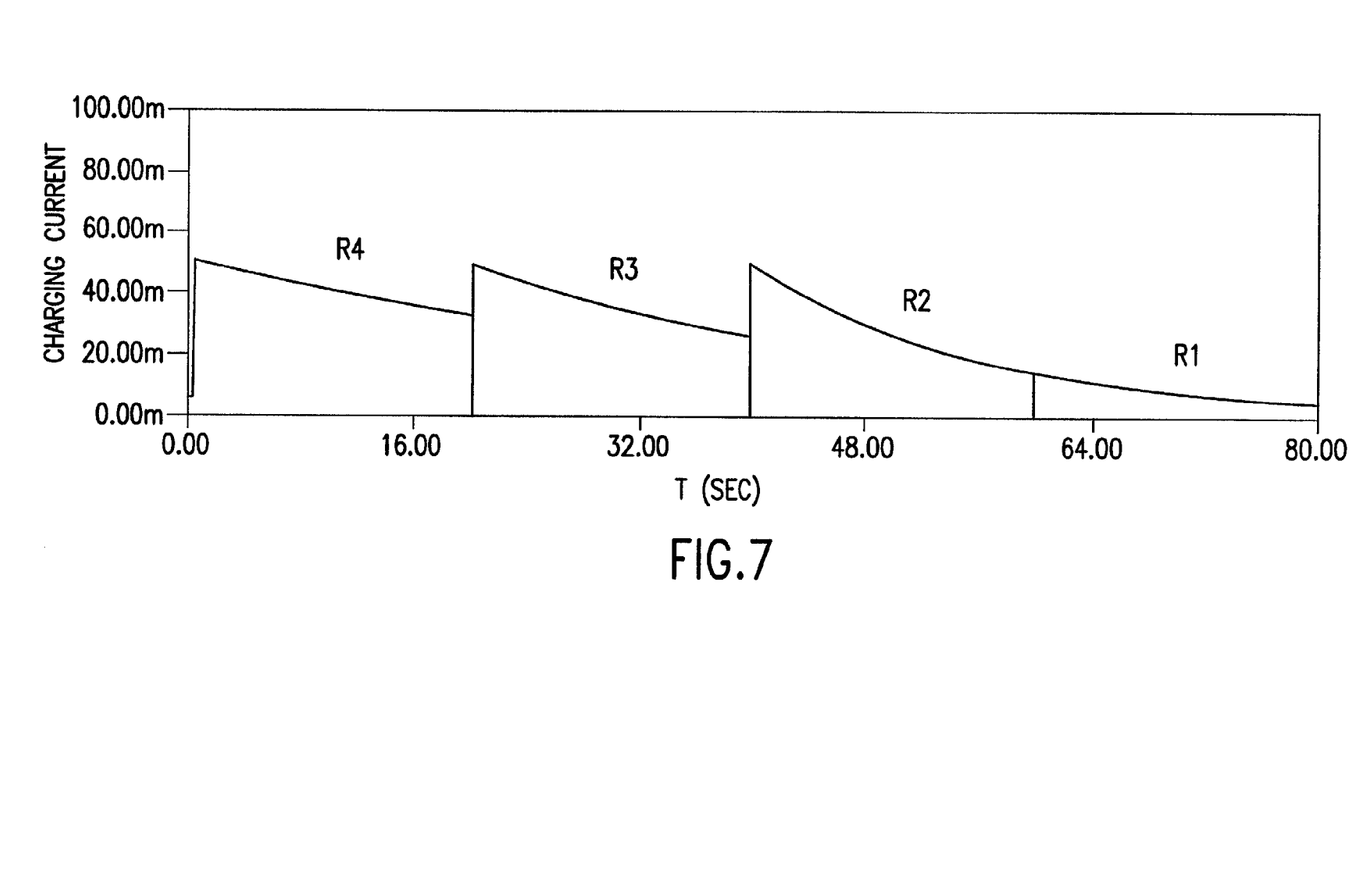
FIG. 7 is a timing diagram of the voltage impressed across the storage capacitor.
Figure 8:
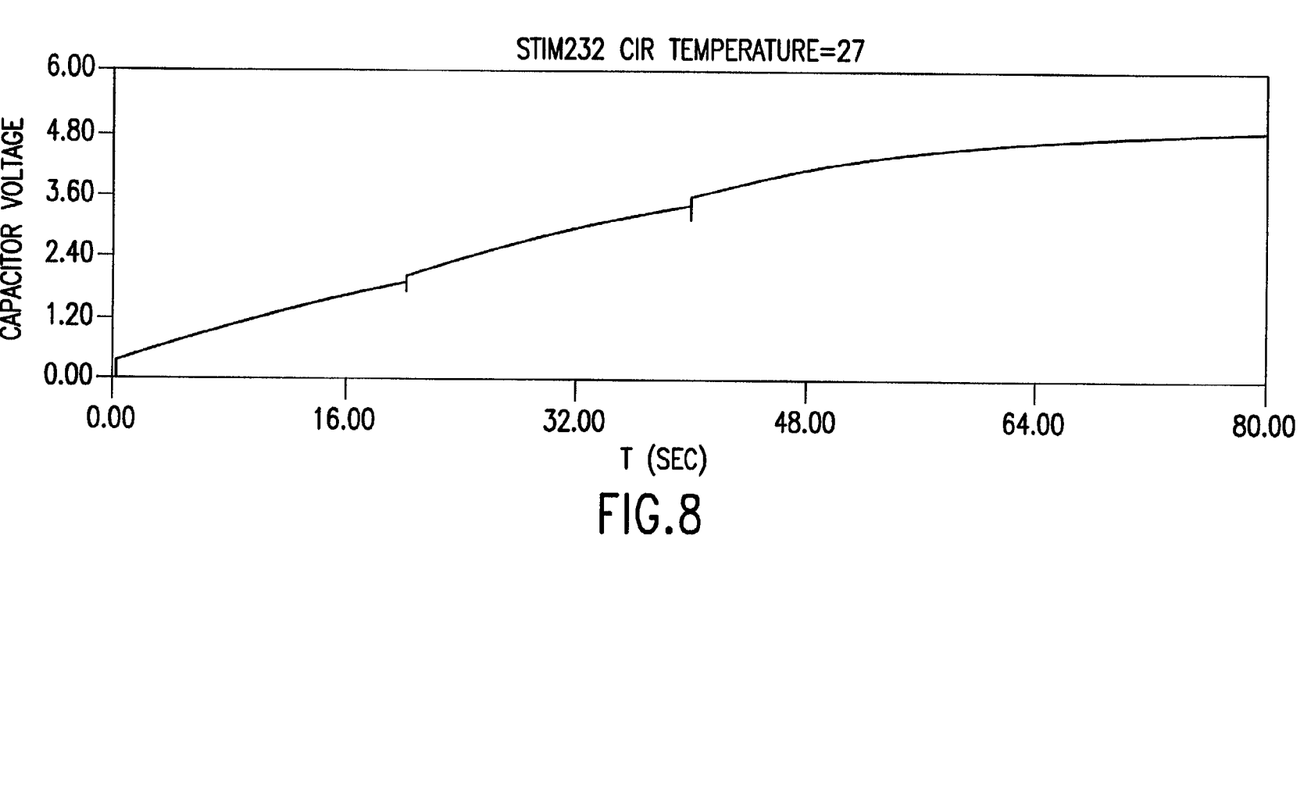
FIG. 8 is a timing diagram showing charging current of the storage capacitor.

As shown in FIGS. 7 and 8, presenting the charging curve for initial power-on, by using the technique of the present invention, a 0.47F capacitor may be fully charged in about 80 seconds from a completely discharged state. This value capacitor will have about 2.3 Ampere-seconds of capacity (to a fully discharged state). Thus, once charged, the storage capacitor 68 will supply the peak current needed by the transmitter circuit 20 without stressing the limited current capability of the RS-232 line.

The transmitter system of the present invention may be powered by the battery or alternatively by the power supply block 64 using, as a raw power source, the host computer. The principles of both systems, presented in previous paragraphs can be combined to build a transmitter, shown in FIG. 4, in which, the capacitor 68, while discharging, supplies current to the resistor 24 of the transmitter circuit 20 to power the operation thereof. The transmitter circuit 20, shown in FIG. 4, operates in the same manner as the transmitter circuit shown in FIGS. 1–3.

The subject transmitter system is capable of generating maximum transmitter RF power while minimizing battery or other power source current drain. The system is suitable for digital data transmission between medical devices located in proximity with the patient's skin, while minimizing the effects of the patient's body on the device operation. Use of frequency feedback control, such as feedback circuit 42, maintains maximum transmitter efficiency while minimizing battery current drain. The novel power supply block 64 for supplying large peak current to a wireless transmitter using a standard RS-232 interface and a large value capacitor permits monitoring the charging current and the time of full charging of the capacitor, as well as to maintain these parameters at predetermined desired levels.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A transmitter system for wireless communication with a remote receiver, comprising:
    a transmitter circuit, said transmitter circuit including a resonant network oscillating at a resonant frequency to generate signals for transmission to the remote receiver,
    current sensing means coupled to said transmitter circuit for sensing current consumed by the same, and
    a controller generating a drive signal and outputting said drive signal to said transmitter circuit to control said resonance frequency thereof, said controller being coupled to said current sensing means to monitor said sensed current and changing said drive signal to adjust said resonance frequency of said resonant network once said sensed current exceeds a predetermined current value to minimize said sensed current consumed by said transmitter circuit.

2. The transmitter system of claim 1, wherein said current sensing means includes an Analog-to-Digital converter.

3. The transmitter system of claim 1, wherein said controller includes a microcontroller.

4. The transmitter system of claim 1, wherein said transmitter circuit further includes first and second pairs of switches forming an H-bridge coupled to said resonant network, said drive signal generated by said controller being fed to said switches of said H-bridge to control switching thereof, thereby controlling said resonant frequency of said resonant network.

5. The transmitter system of claim 4, wherein said drive signal includes first pulses and second pulses generated at a time interval therebetween, said first pulses being fed to said first pair of switches, and said second pulses being fed to said second pair of switches.

6. The transmitter system of claim 5, wherein said interval between said first and second pulses corresponds to a natural resonance frequency of said resonant network when said sensed current remains below said predetermined current value.

7. The transmitter system of claim 6, wherein upon said sensed current exceeding said predetermined current value, said controller changes said interval between said first and second pulses to deviate said resonant frequency of said resonant network from said natural resonant frequency thereof to decrease said sensed current to the value below said predetermined current value.

8. The transmitter system of claim 7, wherein said interval between said first and second pulses is equal to sub-multiples of said natural resonant frequency.

9. The transmitter system of claim 1, wherein said remote receiver includes a medical device implanted in a human body, and wherein said resonant network includes a LC tank and the human body capacitance.

10. The transmitter system of claim 1, further comprising a battery supplying current to said transmitter circuit.

11. The transmitter system of claim 1, further comprising:
a power supply block supplying power to said transmitter circuit, said power supply block comprising:
a current limit switching circuit coupled to the serial port of a host computer, said current limit switching circuit includes a plurality of limiting resistors,
a storage capacitor coupled between an output of said current limit switching circuit and said transmitter circuit, said storage capacitor being charged with charging current supplied from the host computer through said current limit switching circuit, and said storage capacitor supplying discharging current therefrom to said transmitter circuit, and
a feedback circuit coupled between said storage capacitor and said current limit switching circuit, said feedback circuit including:
an analog-to-digital converter coupled to said storage capacitor to monitor the voltage across said storage capacitor, and
a microprocessor coupled between the output of said analog-to-digital converter and said current limit switching circuit, said microprocessor comparing said monitored voltage across said storage capacitor with a predetermined voltage limit value, and switching said current limit switching circuit to an appropriate limiting resistor therein once said voltage limit value has been reached.

12. The transmitter system of claim 11, wherein said analog-to-digital converter further monitors charging current supplied to said storage capacitor during charging period, and wherein said microprocessor switches said current limit switching circuit to a respective limiting resistor once said charging current falls below a predetermined level thereof to keep said charging current at said predetermined level thereof.

13. The transmitter system of claim 11, wherein said microprocessor establishes a switching hysteresis to prevent switch chatter at the crossover points.

14. A transmitter system for wireless communication with a remote receiver, comprising:
a transmitter circuit generating signals and transmitting the generated signals to the remote receiver; and
a power supply block coupled to said transmitter circuit to supply power thereto,
said power supply block comprising:
a. a current limit switching circuit coupled to a host computer to receive input power therefrom, said current limit switching circuit including a plurality of current limiting structures switchable to control charging current output from said current limit switching circuit at an output thereof,
b. a storage capacitor coupled to said output of said current limit switching circuit for being charged with said controlled charging current, and said storage capacitor being further coupled to said transmitter circuit to supply thereto a discharge current of said storage capacitor, and
c. a feed-back circuit coupled between said storage capacitor and said current limit switching circuit, said feed-back circuit being adapted to monitor said charging current supplied to said storage capacitor and to switch said current limit switching circuit to a respective current limiting structure thereof to keep said charging current at a predetermined level thereof for the duration of the charging time.

15. The transmitter system of claim 14, wherein said feed-back circuit is further adapted to monitor voltage impressed across said storage capacitor and to switch said current limit switching circuit to an appropriate current limiting structure thereof to stop charging once said voltage impressed across said storage capacitor has reached a predetermined level thereof.

16. The transmitter system of claim 14, wherein said current limiting structures in said current limiting structures in said current limit switching circuit include a plurality of distinct resistors connected in parallel and a plurality of switches, each of said switches being associated with a respective one of said resistors, said feed-back circuit controlling the state of each of said switches to select a respective resistor for limiting said charging current.

17. The transmitter system of claim 15, wherein said feed-back circuit includes an Analog-to-Digital converter coupled to said storage capacitor for reading said charging current and said voltage impressed across said storage capacitor, and a microprocessor coupled between the output of said Analog-to-Digital converter and said current limit switching circuit, said microprocessor including means for comparing digital data output at said Analog-to-Digital converter to the data corresponding to said predetermined level of said charging current and to said voltage impressed across said storage capacitor, respectively, and for selecting said respective current limiting structure based upon said comparison.

18. The transmitter system of claim 17, wherein said microprocessor further includes means for establishing a predetermined delay between receiving the results of said comparison and actual switching of said current limit switching circuit to prevent switch chatter at crossover points.

19. The transmitter system of claim 14, wherein said current limit switching circuit receives said input power from the serial port of the host computer.

20. The transmitter system of claim 14, further comprising means for impeding supply of the charging current to said storage capacitor prior to substantially complete discharge state thereof.

21. The transmitter system of claim 14, wherein said transmitter circuit includes a resonant network oscillating at a resonant frequency to generate signals for transmission to the remote receiver, and wherein said transmitter system further comprises:
 a. current sensing means coupled to said transmitter circuit for sensing current consumed by the same, and
 b. a controller generating a drive signal to said transmitter circuit to control said resonance frequency thereof, said controller being coupled to said current sensing means to monitor said sensed current and changing said drive signal to adjust said resonance frequency of said transmitter circuit once said sensed current exceeds a predetermined current value to minimize said sensed current consumed by said transmitter circuit.

22. The transmitter system of claim 21, wherein said current sensing means includes an Analog-to-Digital converter.

23. The transmitter system of claim 21, wherein said controller includes a microcontroller.

24. The transmitter system of claim 21, wherein said transmitter circuit further includes first and second pairs of switches forming an H-bridge coupled to said resonant network, said drive signal generated by said controller being fed to said switches of said H-bridge to control switching thereof, thereby controlling said resonant frequency of said transmitter circuit.

25. The transmitter system of claim 24, wherein said drive signal includes first pulses and second pulses generated at a time interval, said first pulses being fed to said first pair of switches, and said second pulses being fed to said second pair of switches.

26. The transmitter system of claim 25, wherein said interval between said first and second pulses corresponds to a natural resonance frequency of said resonant network when said sensed current remains below said predetermined current value.

27. The transmitter system of claim 26, wherein upon said sensed current exceeds said predetermined current value, said controller changes said interval between said first and second pulses to deviate said resonant frequency of said transmitter circuit from said natural resonant frequency to decrease said sensed current to the value below said predetermined current value.

28. The transmitter system of claim 21, wherein said interval between said first and second pulses is equal to sub-multiples of said natural resonant frequency.

29. The transmitter system of claim 21, wherein said receiver includes a medical device implanted into a human body, and wherein said resonant network includes LC tank and the human body capacitance.

* * * * *